United States Patent [19]

Krumkalns

[11] 4,116,665

[45] * Sep. 26, 1978

[54] METHOD OF REGULATING THE GROWTH OF AQUATIC WEEDS WITH PYRIDINE DERIVATIVES

[75] Inventor: Eriks V. Krumkalns, Indianapolis, Ind.

[73] Assignee: Eli Lilly and Company, Indianapolis, Ind.

[*] Notice: The portion of the term of this patent subsequent to Aug. 23, 1994, has been disclaimed.

[21] Appl. No.: 833,541

[22] Filed: Sep. 15, 1977

Related U.S. Application Data

[63] Continuation-in-part of Ser. No. 673,030, Apr. 2, 1976, abandoned.

[51] Int. Cl.$^2$ .............................................. A01N 9/22
[52] U.S. Cl. ............................................ 71/66; 71/94
[58] Field of Search ...................................... 71/66, 94

[56] References Cited

U.S. PATENT DOCUMENTS

| 3,244,722 | 4/1966 | Johnson | 71/66 X |
| 3,655,359 | 4/1972 | Krumkalns et al. | 71/94 |
| 3,746,531 | 7/1973 | Doherty | 71/66 X |

*Primary Examiner*—Catherine L Mills
*Attorney, Agent, or Firm*—Dwight E. Morrison; Arthur R. Whale

[57] ABSTRACT

A method of regulating the growth of submerged and floating aquatic weeds which comprises adding a 3-substituted pyridinemethane, pyridinemethanol, or derivative thereof, to a body of water containing the submerged and floating aquatic weeds to be regulated, in quantities sufficient to regulate the growth of the said submerged and floating aquatic weeds. The disclosure also relates to novel compositions for carrying out the method.

13 Claims, No Drawings

METHOD OF REGULATING THE GROWTH OF AQUATIC WEEDS WITH PYRIDINE DERIVATIVES

CROSS-REFERENCE

This application is a continuation-in-part of my copending application Ser. No. 673,030, filed Apr. 2, 1976 now abandoned.

BACKGROUND OF THE INVENTION

1. Field of the Invention

The field of the invention relates to the regulation of the growth of aquatic weeds in canals, rivers, ponds, lakes and impoundments.

2. Description of the Prior Art

The problems of controlling or regulating the growth of organisms in aqueous systems are series and growing in severity. Submerged aquatic weeds, for example, cause major problems in water distribution and irrigation systems. The growth of such weeds in irrigation canals greatly reduces the conductivity and capacity of such systems with resulting substantial economic loss. Large sums are spent in the mechanical and other methods of removal of weed growths from irrigation canals, especially in the western parts of the United States. Because of the great difficulties involved in the mechanical removal of weeds and other undesired forms of aquatic life from irrigation canals, ponds, lakes, impoundments, etc., it has been proposed to utilize chemical control. Accordingly, various types of chemicals have been added to such bodies of water.

However, with the growing emphasis on conservation, current efforts are directed toward regulating the growth, that is limiting or inhibiting the amount of growth accomplished by the naturally occurring submerged or floating aquatic weeds, without killing those weeds. This approach is being taken in order to continue to provide the natural environment for fish and other forms of marine life. A further reason is to avoid the masses of dead and rotting aquatic weeds which result when said weeds are killed by means of an aquatic herbicide, since the decomposition of the weeds decreases the amount of available oxygen present in the water. Such decaying matter, when it occurs in reservoirs and/or streams from which drinking water for cities is obtained, makes purification of the water much more difficult. Such decaying vegetation also gives off an unpleasant odor when it collects in a body of water. Thus, a control of the amount of growth rather than a destruction of the submerged aquatic weeds serves to overcome both pollution of the water and pollution of the air.

In the prior art, Krumkalns et al., U.S. Pat. No. 3,655,359 Apr. 11, 1972), teach and claim the use of substituted 3-pyridylmethanes for eliminating germinating weed grasses and broadleaf weeds selectively from crop plants such as corn, cotton, and soybeans, and their close relatives in the plant kingdom. I have found many of the compounds appearing in this reference useful for the regulation of the growth of aquatic weeds and they come within the scope of the compounds used in the present invention. There is no teaching in the reference that the compounds disclosed therein would act to control the growth of submerged or floating aquatic weeds.

Also in the prior art, Krumkalns et al., U.S. Pat. No. 3,744,988 (July 10, 1973), teach and claim the use of substituted 3-pyridylmethanes in a method for inhibiting sucker growth to tobacco plants. This patent is a division of U.S. Pat. No. 3,655,359, supra, and includes in its disclosure many of the same compounds disclosed in that patent. There is no teaching in the reference that the compounds disclosed therein would act to control the growth of submerged or floating aquatic weeds.

Van Heyningen, U.S. Pat. No. 3,396,224 (Aug. 6, 1968), teaches and claims a method of controlling fungi pathogenic to plants by contacting the fungus-susceptible plant with a fungicidal amount of a 3-pyridylmethane derivative, mainly a 3-pyridinemethanol. I have found many of the compounds disclosed in this reference active as aquatic plant growth regulators, and they are included within the scope of the instant application. There is no teaching in this reference that the compounds disclosed would be active as aquatic growth regulators of submerged or floating aquatic weeds.

Van Heyningen et al., U.S. Pat. No. 3,397,273 (Aug. 13, 1968), teach and claim a method for protecting plants from attack by phytopathogenic fungi by treating the plants with a fungicidally-effective amount of a 3-pyridylmethane. Some of the compounds disclosed by this reference have now been found by me to be active as aquatic growth regulators, and their use for that purpose is disclosed and claimed in the instant application. This reference makes no suggestion that the therein disclosed compounds would be active as growth regulators of submerged or floating aquatic weeds.

Krumkalns, U.S. Pat. No. 3,335,148 (Aug. 8, 1967), discloses and claims the 9-(3-pyridyl) derivative of fluorene, 9-fluorenol, xanthene, 9-xanthenol, and the corresponding nonphytotoxic acid addition salts thereof. The compounds are alleged to posses antifungal and antibacterial activities. I have now found some of the compounds to be active as aquatic growth regulators, and such compounds are included for that use in the instant application. There is no teaching or suggestion in this reference that the compounds would be active as growth regulators of submerged or floating aquatic weeds.

Yet another reference, Krumkalns, U.S. Pat. No. 3,361,753 (Jan. 2, 1968), is directed to 9-(3-pyridyl)-thioxanthene and thioxanthol derivatives, active as plant antifungal agents and as antibacterial agents. There is no teaching that the compounds of this reference would be active as regulators of the growth of submerged or floating aquatic weeds.

Another reference is German Pat. No. 1,935,292, also identified by Derwent No. 04548S, which patent teaches and claims a means for controlling plant growth, that is restraining growth and influencing the habits of higher plants, influencing blossom and fruit formation, checking the growth of grass, and the like, using triarymethylimidazoles, -pyrazoles, and -triazoles, or their salts. One of the aryl groups is taught as pyridyl. The reference does not include use on aquatic weeds or plants.

Yet another reference is British Patent No. 1,274,578, also identified by Derwent No. 23143S. This reference teaches plant growth regulators containing N-benzylimidazoles, wherein one of the substituents is a pyridyl group. These compounds are alleged to be plant growth regulators capable of inhibiting or accelerating growth, flowering, and fruiting, according to the amount applied. Certain of the compounds are also alleged to be plant fungicides and bactericides.

SUMMARY OF THE INVENTION

The present invention relates to a method of inhibiting the growth of submerged and floating aquatic weeds by adding to the water containing such submerged and floating aquatic weeds a growth-regulating and non-herbicidal amount of a 3-substituted pyridinemethane, pyridinemethanol, or derivative thereof.

DESCRIPTION OF THE PREFERRED EMBODIMENT

This invention relates to a novel method for inhibiting the growth of submerged and floating aquatic weeds. More particularly, this invention relates to a novel method and compositions for regulating the growth of submerged and floating aquatic weeds which comprises adding to the water containing said weeds a growth-regulating and non-herbicidal amount of a compound of the formula

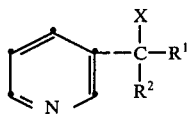

(I)

wherein

X is hydrogen, hydroxyl, halo, $C_1$-$C_3$ alkoxy, $C_1$-$C_6$ alkylthio, cyclohexylthio, 4-chlorophenylthio, —$N(R^3)_2$, acetamido, imidazol-1-yl, morpholino, or cyano;

$R^1$ is hydrogen, $C_1$-$C_9$ alkyl, ethynyl, $C_3$-$C_6$ cycloalkyl, benzyl, phenyl, or monohalophenyl;

$R^2$ is $C_1$-$C_9$ alkyl, $C_3$-$C_6$ cycloalkyl, cyclohexylmethyl, cyclohexylethyl, phenyl, monohalophenyl, dihalophenyl, 3,4-(methylenedioxy)phenyl, trifluoromethylphenyl, p-cumenyl, tolyl, phenoxyphenyl, phenoxy($C_1$-$C_4$)alkyl, benzyl, $C_1$-$C_4$ alkoxyphenyl, pentafluorophenyl, xylyl, 2-thienyl, 3-pyridyl, 1,3-dioxan-5-yl, or 5-methyl-1,3-dioxan-5-yl;

$R^1$ and $R^2$, when taken together with the carbon atom to which they are attached, form 2,6-dimethylcyclohexan-1-yl, 9-fluorenyl, 10,11-dihydro-5H-dibenzo[a,d]cyclohepten-5-yl, 9-xanthenyl, 5H-dibenzo[a,d]cyclohepten-5-yl, or 9-thioxanthenyl;

$R^3$ is hydrogen or $C_1$-$C_6$ alkyl; and the nonphytotoxic acid addition salts thereof.

In the above formula, $C_1$-$C_3$ alkoxy can be methoxy, ethoxy, isopropoxy, and propoxy.

$C_1$-$C_6$ Alkylthio can be methylthio, ethylthio, isopropylthio, n-propylthio, n-butylthio, n-pentylthio, n-hexylthio, and the like.

The $C_1$-$C_9$ alkyl groups are saturated straight or branched-chain alkyl and can be illustratively methyl, ethyl, propyl, isopropyl, n-butyl, s-butyl, t-butyl, n-amyl, isoamyl, s-amyl, n-hexyl, isohexyl, s-hexyl, n-heptyl, isoheptyl, s-heptyl, n-octyl, isooctyl, s-octyl, n-nonyl, isononyl, s-nonyl, and the like.

3-$C_6$ Cycloalkyl can be, illustratively, saturated monocyclic cycloalkyl such as cyclopropyl, cyclobutyl, cyclopentyl and cyclohexyl. Monohalophenyl can be, illustratively, o-chlorophenyl, p-chlorophenyl, p-fluorophenyl, p-bromophenyl, p-iodophenyl, m-chlorophenyl, and the like.

Dihalophenyl can be 2,4-difluorophenyl, 2,4-dichlorophenyl, 2,4-dibromophenyl, 3,4-difluorophenyl, 3,4-dichlorophenyl, 3,4-dibromophenyl, 4-chloro-3-fluorophenyl, 3,5-difluorophenyl, 3,5-dichlorophenyl, 3,5-dibromophenyl, and the like.

Phenoxy($C_1$-$C_4$) alkyl can be phenoxymethyl, phenoxyethyl, phenoxypropyl, and phenoxybutyl.

$C_1$-$C_4$ Alkoxyphenyl can be methoxyphenyl, ethoxyphenyl, propoxyphenyl and butoxyphenyl.

Xylyl is 3,4-xylyl, 2,3-xylyl, 2,4-xylyl, 3,5-xylyl, 2,5-xylyl or 2,6-xylyl.

Halo or halogen is chlorine, bromine, iodine, or fluorine.

The compounds coming within the scope of the above generic formula are effective for regulating the growth of aquatic weeds when applied to the locus of the weeds at a concentration in the range of from about 0.25 to about 10 ppm., suitably at a concentration in the range of from about 0.25 to about 2 ppm.

The compounds preferred for use in the novel method of this invention are of the formula (I) above wherein X is hydrogen, hydroxyl, or methoxy;

$R^1$ is hydrogen, $C_1$-$C_8$ alkyl, $C_3$-$C_6$ cycloalkyl, or phenyl;

$R^2$ is $C_1$-$C_8$ alkyl, cyclohexylmethyl, cyclohexyl, phenyl, 4-fluorophenyl, 4-chlorophenyl, 4-methoxyphenyl, p-tolyl, or 4-phenoxy-n-butyl;

$R^1$ and $R^2$, when taken together with the carbon atom to which they are attached, form 9-fluorenyl, 9-xanthenyl, or 10,11-dihydro-5H-dibenzo[a,d]cyclohepten-5-yl; and the nonphytotoxic acid addition salts thereof.

The compounds more preferred for use in the novel method of this invention are those of the formula (I) above wherein X is hydrogen, hydroxyl or methoxy;

$R^1$ is $C_3$-$C_8$ alkyl, cyclopropyl, cyclohexyl, or phenyl;

$R^2$ is $C_4$-$C_7$ alkyl, 4-chlorophenyl, 4-fluorophenyl, 4-methoxyphenyl, p-tolyl, cyclohexylmethyl, phenyl, and 4-phenoxy-n-butyl;

$R^1$ and $R^2$, when taken together with the carbon to which they are attached, form 9-fluorenyl; and the nonphytotoxic acid addition salts thereof.

The compounds most preferred for use in the novel method of this invention are those of the formula (I) above wherein X is hydroxyl;

$R^1$ is isopropyl, cyclopropyl, isobutyl, t-butyl, or phenyl;

$R^2$ is n-hexyl, phenyl, 4-fluorophenyl, 4-methoxyphenyl, or 4-chlorophenyl; and the nonphytotoxic acid addition salts thereof.

The compound of choice for use in this novel method is selected from the group consisting of α-(4-chlorophenyl)-α-isopropyl-3-pyridinemethanol, α-isopropyl-α-(4-methoxyphenyl)-3-pyridinemethanol, and α-(t-butyl)-α-(4-fluorophenyl)-3-pyridinemethanol.

The compounds useful in this invention are conveniently prepared by methods well-known to the art. Thus, many of the 3-pyridinemethanols and derivatives thereof are described and made available through the teachings of Van Heyningen, U.S. Pat. No. 3,396,224 (Aug. 6, 1968); and many of the 3-pyridinemethane derivatives are disclosed and made available through the teachings of Van Heyningen et al., U.S. Pat. No. 3,397,273 (Aug. 13, 1968). The 9-(3-pyridyl) derivatives of fluorene, 9-fluorenol, xanthene, and 9-xanthenol, and methods for their preparation, are disclosed by Krumkalns, U.S. Pat. No. 3,335,148 (Aug. 8, 1967); while the 9-(3-pyridyl)thioxanthene and thioxanthenol derivatives, together with methods for their preparation, are taught in Krumkalns, U.S. Pat. No. 3,361,753 (Jan. 2, 1968). The compounds of the generic formula wherein X = phenylthio, N,N-dialkyl, or piperidino, and methods for their preparation are disclosed by Krumkalns et al., U.S. Pat. No. 3,849,423 (Nov. 19, 1974). In particular, the α,α-dialkyl-substituted 3-pyridinemethanols are prepared according to the teaching of Wibaut et al., Rec. Trav. Chim., 77, 1057 (1958). Those compounds wherein X is $C_1$-$C_3$ alkoxy, cyano, acetamido, chlorophenylthio, phenylthio, cyclohexylthio or $C_1$-$C_6$ alkylthio, are prepared by methods disclosed in the above-cited references.

Suitable nonphytotoxic acid addition salts of the pyridine bases represented by the above formula can be prepared by methods well known to the art employing, for example, the following acids: hydrochloric, hydrobromic, sulfuric, phosphoric, methanesulfonic, and the like.

The intermediate compounds not commercially available, i.e., ketones, are synthesized by methods well known in the art, and these syntheses are described in the following preparations.

Preparation 1

Isopropyl m-tolyl ketone

In a three-neck round-bottom flask fitted with a mechanical stirrer, and a reflux condenser, and protected from moisture, there was placed 300 ml. of tetrahydrofuran, to which was added 10 g. of magnesium shavings. The mixture was then heated to refluxing. A catalytic amount of iodine was added, followed by the dropwise addition of 75 g. of m-bromotoluene. The Grignard reagent which was thus formed was a slate gray color. The reaction was held at reflux temperature until the magnesium had completely reacted. The reaction mixture was then cooled and 14 g. of isobutyronitrile was added dropwise to the mixture. The reaction product mixture was then heated to reflux for several hours. At the end of the heating period, the reaction product mixture was cooled and ammonium chloride hydrate was added, followed by concentrated hydrochloric acid, until the solution was acidic. The organic layer was separated, dried over anhydrous sodium sulfate, and concentrated in vacuo. There was obtained an oil which weighed about 38 g., and which was identified by NMR and IR spectra as isopropyl m-tolyl ketone.

Following the general procedure of Preparation 1, additional intermediate ketones were prepared. The principal starting materials, and the weights thereof used in the syntheses, are set forth hereinafter.

Preparation 2

Isopropyl 3,4-xylyl ketone, having a b.p. of about 122°–124° C./6-8 mm., from 74 g. of 3,4-xylylbromide and 28 g. of isobutyronitrile. Yield 32 g.

Preparation 3

4-Chlorophenyl isopropyl ketone, as an oil, from 690 g. of isobutyronitrile and 1915 g. of 4-chlorophenylbromide. Yield 1370 g.

Preparation 4 t-Butyl 4-fluorophenyl ketone, from 25 g. of trimethylacetonitrile and 60 g. of p-fluorophenyl bromide. Yield 20 g.

Preparation 5 t-Butyl 4-chlorophenyl ketone, having a boiling point of about 82-89° C./0.12 mm., and weighing about 40 g., from 200 g. of trimethylacetonitrile and 461 g. of 4-chlorobromobenzene.

Preparation 6

Isopropyl 3,4-methylenedioxyphenyl ketone

The Grignard reagent prepared from 25 g. of isopropylbromide and 5 g. of magnesium turnings in 100 ml. of ether was allowed to react with 30 g. of 3,4-methylenedioxybenzaldehyde, and the resulting isopropyl-3,4-methylenedioxyphenylcarbinol was isolated and used without purification in the next step of the reaction.

The carbinol thus prepared was dispersed in about 200 ml. of glacial acetic acid with stirring, and to the mixture was added 20 g. of chromium trioxide dissolved in about 30 ml. of water. The addition was carried out carefully and the reaction temperature was kept below 80° C. Stirring of the mixture was continued for about 4 hours. The reaction product mixture was cooled and poured onto a mixture of crushed ice and aqueous 50 percent sodium hydroxide solution, and the pH of the mixture was adjusted to pH 8. The mixture was extracted with large volumes of ether and the ether extracts combined and washed with dilute aqueous sodium hydroxide solution. The ether solution was dried and concentrated in vacuo to leave a residue. The residue was chromatographed over a silica column, using benzene as solvent and eluant, to yield 20 g. of product, which was identified by NMR and infrared spectrum as isopropyl 3,4-methylenedioxyphenyl ketone.

Preparation 7

5-(4-Chlorobenzoyl)-5-methyl-1,3-dioxane

Following the generalized procedures taught by (a) Terada, Nippon Kagan Zasshi. 81, 612 (1960), Chem. Abst. 56, 1446 (1962); (b) British Patent No. 1,148,247, Chem. Abst. 71, 61394u (1969); (c) Wesslen, Acta. Chem. Scand. 23, 1033 (1969), a mixture of 50.7 g. of 4-chloropropiophenone, 90 g. of paraformaldehyde, 128 g. of $BF_3$·etherate, and 300 ml. of acetonitrile was allowed to react, and there was isolated 10.5 g. of product having a melting point of about 108°–109° C., after recrystallization from petroleum ether. The product was identified by NMR spectrum as 5-(4-chlorobenzoyl)-5-methyl-1,3-dioxane.

Following the same general procedure described in Preparation 7, additional intermediate ketones were prepared. The principal starting materials, and the weights thereof used in the syntheses, are set forth hereinafter.

Preparation 8

5-Benzoyl-5-methyl-1,3-dioxane, having a melting point of about 79°–81° C., and weighing 6.5 g., from 13.4 g. of propiophenone, 9 g. of paraformaldehyde, and 93 g. of $BF_3$·etherate.

Preparation 9

5-(2,4-Dichlorobenzoyl)-1,3-dioxane, having a boiling point of about 120-140° C./0.3 mm., from 50 g. of 2,4-dichloroacetophenone, 180 g. of paraformaldehyde, and 114 g. of $BF_3$·etherate.

| Analyses calculated for $C_{11}H_{10}Cl_2O_3$: | | |
|---|---|---|
| | Theoretical | Found |
| C | 50.59% | 50.74% |
| H | 3.86 | 3.87 |
| N | 27.16 | 27.41 |

Compounds coming within the scope of the structural formula above, and not previously prepared, and not disclosed in the references cited supra, are synthesized following the same general procedures taught in those references. These compounds and their preparation and identity are described in the following examples.

EXAMPLE 1

α-Isopropyl-α-(3,4-xylyl)-3-pyridinemethanol

In a multi-neck round-bottom flask equipped with a dropping funnel, a gas-inlet tube, a mechanical stirrer, and protected from moisture, there was placed about 500 ml. of anhydrous ether, and, while dry nitrogen was introduced into the flask through the gas-inlet tube, the whole was cooled at about −70° C. To this cold ether, there was added in a single portion, 45 ml. of commercially-available (2.1-2.3 molar) hexane suspension of n-butyllithium. The mixture was stirred and cooled to about −70° C. There was then added dropwise, with stirring, 13.5 g. of 3-bromopyridine, while the temperature of the mixture was held at about −70° C., plus or minus 3°. The mixture was stirred for about 0.5 hour after addition of the 3-bromopyridine was completed, and then 15 g. of isopropyl 3,4-xylyl ketone was added dropwise with continued stirring. The reaction mixture was allowed to stir overnight and warm to ambient room temperature during that time. The reaction product mixture was worked up by adding water, separating the organic layer and extracting the aqueous layer several times with ether. The original ether layer and the ether extracts were combined and dried over anhydrous sodium sulfate. The drying agent was filtered off and most of the ether removed in vacuo.

The material which crystallized from the ether was filtered off and again recrystallized from ether to yield product weighing 11 g., and having a melting point of about 109°–110° C. The product was identified by NMR spectrum and elemental analyses as α-isopropyl-α-(3,4-xylyl)-3-pyridine-methanol.

| Analyses calculated for $C_{17}H_{21}NO$: | | |
|---|---|---|
| | Theoretical | Found |
| C | 79.96% | 79.70% |
| H | 8.29 | 8.34 |
| N | 5.49 | 5.71 |

Following the general procedure of Example 1, additional compounds were prepared and identified. The compounds, together with the principal starting materials and weights thereof used in the preparations, are listed in the examples set forth hereinafter.

EXAMPLE 2

α-Isopropyl-α-(p-tolyl)-3-pyridinemethanol, having a melting point of about 126–127° C., from 16 g. of 3-bromopyridine and 16.2 g. of isopropyl p-tolyl ketone. Yield: 8.5 g.

| Analyses calculated for $C_{16}H_{19}NO$: | | |
|---|---|---|
| | Theoretical | Found |
| C | 79.62% | 79.73% |
| H | 7.93 | 7.71 |
| N | 5.80 | 5.70 |

EXAMPLE 3

α-Isopropyl-α-(m-tolyl)-3-pyridinemethanol, having a melting point of about 122–123° C., from 16 g. of 3-bromopyridine and 16.2 g. of isopropyl m-tolyl ketone. Yield: 9 g.

| Analyses calculated for $C_{16}H_{19}NO$: | | |
|---|---|---|
| | Theoretical | Found |
| C | 79.62% | 79.42% |
| H | 7.93 | 7.72 |
| N | 5.80 | 5.83 |

EXAMPLE 4

α-(4-Chlorophenyl)-α-isopropyl-3-pyridinemethanol, having a melting point of about 143° C., from 16 g. of 3-bromopyridine and 18 g. of 4-chlorophenyl isopropyl ketone. Yield: 11 g.

| Analyses calculated for $C_{15}H_{16}ClNO$: | | |
|---|---|---|
| | Theoretical | Found |
| C | 68.83% | 68.38% |
| H | 6.16 | 6.00 |
| N | 5.35 | 5.31 |

EXAMPLE 5

α-(t-Butyl)-α-(4-fluorophenyl)-3-pyridinemethanol, having a melting point of about 150° C., from 48 g. of 3-bromopyridine and 56 g. of t-butyl p-fluorophenyl ketone. Yield: 6 g.

| Analyses calculated for $C_{16}H_{18}FNO$: | | |
|---|---|---|
| | Theoretical | Found |
| C | 74.11% | 73.89% |
| H | 7.00 | 6.90 |
| N | 5.40 | 5.18 |

EXAMPLE 6

α-(1-Methylpropyl)-α-pentyl-3-pyridinemethanol, as an oil, from 16 g. of 3-bromopyridine and 16 g. of 3-methyl-4-nonanone. Yield 8.9 g., after purification over a silica column.

| Analyses calculated for $C_{15}H_{25}NO$: | | |
|---|---|---|
| | Theoretical | Found |
| C | 76.55% | 76.68% |
| H | 10.71 | 10.59 |
| N | 5.95 | 5.92 |

EXAMPLE 7

α-Heptyl-α-isopropyl-3-pyridinemethanol, as an oil, from 16 g. of 3-bromopyridine and 17 g. of 2-methyl-3-decanone. The oil was purified over a silica gel column. Yield 10.9 g.

| Analyses calculated for $C_{16}H_{27}NO$: | | |
|---|---|---|
| | Theoretical | Found |
| C | 77.06% | 77.28% |
| H | 10.91 | 10.86 |
| N | 5.61 | 5.51 |

EXAMPLE 8

α-Isopropyl-α-[3,4-(methylenedioxy)phenyl]-3-pyridinemethanol, having a melting point of about 161° C., and weighing about 2 g., from 20 g. of isopropyl 3,4-methylenedioxyphenyl ketone and 16 g. of 3-bromopyridine. The compound was identified by NMR spectrum.

EXAMPLE 9

α-(Cyclohexylmethyl)-α-(n-heptyl)-3-pyridinemethanol, as an oil, from 24 g. of 3-bromopyridine and 35 g. of cyclohexylmethyl n-heptyl ketone. The oil was purified by chromatographing it over a silica gel column. Yield 27 g. The compound was identified by NMR spectrum and thin-layer chromatography.

EXAMPLE 10

α-(4-Chlorophenyl)-α-(5-methyl-1,3-dioxan-5-yl)-3-pyridinemethanol hydrochloride, having a melting point of about 218° C. (dec), from 12 g. of 5-(4-chlorobenzoyl)-5-methyl-1,3-dioxane and 15.8 g. of 3-bromopyridine. Weight = 8 g.

| Analyses calculated for $C_{17}H_{18}NO_3Cl \cdot HCl$: | | |
|---|---|---|
| | Theoretical | Found |
| C | 57.31% | 57.32% |
| H | 5.38 | 5.48 |
| N | 3.93 | 4.17 |
| Cl | 19.91 | 19.69 |

EXAMPLE 11

α-Phenyl-α-(5-methyl-1,3-dioxan-5-yl)-3-pyridinemethanol hydrochloride, having a melting point of about 225°-227° C. (dec.), from 10.3 g. of 5-benzoyl-5-methyl-1,3-dioxane and 15.8 g. of 3-bromopyridine.

| Analyses calculated for $C_{17}H_{19}NO_3 \cdot HCl$: | | |
|---|---|---|
| | Theoretical | Found |
| C | 63.45% | 63.66% |
| H | 6.26 | 6.35 |
| N | 4.35 | 4.57 |

EXAMPLE 12

α-(2,4-Dichlorophenyl)-α-(1,3-dioxan-5-yl)-3-pyridinemethanol, having a melting point of about 164°-165° C., weighing about 1.5 g., from 10.5 g. of 5-(2,4-dichlorobenzoyl)-1,3-dioxane and 15.8 g. of 3-bromopyridine.

| Analyses calculated for $C_{16}H_{15}Cl_2NO_3$: | | |
|---|---|---|
| | Theoretical | Found |
| C | 56.48% | 56.61% |
| H | 4.44 | 4.60 |
| N | 4.12 | 3.93 |
| Cl | 20.80 | 20.58 |

EXAMPLE 13

α-t-Butyl-α-(4-chlorophenyl)-3-pyridinemethanol, having a melting point of about 136°-141° C., and weighing 120 g., from 111 g. of 3-bromopyridine and 138 g. of t-butyl 4-chlorophenyl ketone. Identified by NMR spectrum.

EXAMPLE 14

α-(t-Butyl)-α-chloro-α-(4-fluorophenyl)-3-pyridinemethane hydrochloride

A solution was prepared of 34 g. of α-(t-butyl)-α-(4-fluorophenyl)-3-pyridinemethanol in 300 ml. of benzene, and there was slowly added to the solution 16 g. of thionyl chloride. When addition was complete, the solution was refluxed for about 2 hours. The reaction mixture was then cooled and filtered. The solid on the filter was washed with benzene. Additional material was obtained by concentrating the filtrate to dryness, leaving a residual solid which was also washed with benzene. The total amount of solid product collected was 37 g. It had a melting point of about 190°-191° C., and was identified by NMR spectrum and elemental analyses as α-(t-butyl)-α-chloro-α-(4-fluorophenyl)-3-pyridinemethane hydrochloride.

| Analyses calculated for $C_{16}H_{17}ClFN \cdot HCl$: | | |
|---|---|---|
| | Theoretical | Found |
| C | 69.19% | 69.10% |
| H | 6.17 | 5.88 |
| N | 5.04 | 5.00 |

EXAMPLE 15

α-(t-Butyl)-α-(4-fluorophenyl)-α-methoxy-3-pyridinemethane

A solution of sodium methylate in methanol was prepared by adding 1 g. of metallic sodium to 150 ml. of absolute methanol in a flask protected from atmospheric moisture. There was then added to the sodium methylate solution, 4 g. of α-(t-butyl)-α-chloro-α-(4-fluorophenyl)-3-pyridinemethane hydrochloride (prepared in Example 14). The reaction mixture was refluxed for about 2 hours and then stirred overnight at ambient room temperature. The reaction product mixture was worked up by concentrating it at reduced pressure. To the residue thus obtained, there was added methylene dichloride and water. The methylene dichloride layer was separated and the aqueous layer was again extracted with methylene dichloride. The original methylene dichloride layer was combined with the extracts, and dried over anhydrous sodium sulfate. The drying agent was filtered off and the filtrate was concentrated in vacuo. The oil that was left as a residue was chromatographed over a silica gel column, elution being accomplished with a mixture containing 85 percent toluene and 15 percent acetone by volume. There was collected 2.5 g. of an oil identified by NMR spectrum and elemental analyses as α-(t-butyl)-α-(4-fluorophenyl)-α-methoxy-3-pyridinemethane.

| Analyses calculated for $C_{17}H_{20}FNO$: | | |
|---|---|---|
| | Theoretical | Found |
| C | 74.70% | 74.50% |
| H | 7.39 | 7.30 |

-continued

| Analyses calculated for $C_{17}H_{20}FNO$: | | |
|---|---|---|
| | Theoretical | Found |
| N | 5.12 | 4.92 |

EXAMPLE 16

α-(t-Butyl)-α-(4-fluorophenyl-α-propoxy-3-pyridinemethane

A solution of sodium propylate was prepared from 1 g. of metallic sodium and 50 ml. of n-propanol and was added to 3 g. of α-(t-butyl)-α-chloro-α-(4-fluorophenyl)-3-pyridinemethane in 50 ml. of propanol. The mixture was then refluxed for about 3 hours and stirred overnight at ambient room temperature. The reaction product mixture was worked up by concentrating it to dryness in vacuo. The residual oil was poured over a silica gel column and elution was accomplished with 20 percent acetone in benzene solution. About 800 mg. of an oil was isolated and identified by NMR spectrum and elemental analyses as α-(t-butyl)-α-(4-fluorophenyl)-α-propoxy-3-pyridinemethane.

| Analyses calculated for $C_{19}H_{24}FNO$: | | |
|---|---|---|
| | Theoretical | Found |
| C | 75.71% | 75.50% |
| H | 8.03 | 7.84 |
| N | 4.65 | 4.42 |

EXAMPLE 17

9-Methoxy-9-(3-Pyridyl)fluorene

The 9-(3-pyridyl)-9-fluorenol was prepared, following the procedure set forth in Krumkalns, U.S. Pat. No. 3,335,148 (Aug. 8, 1967), and was used in the following synthesis.

A mixture of 3 g. of 9-(3-pyridyl)-9-fluorenol, 10 g. of thionyl chloride, and 200 ml. of benzene was allowed to react in the same manner as described in Example 14 above. After refluxing for about 2 hours, the reaction product mixture was cooled and the solvent and excess thionyl chloride were removed in vacuo. To the residue was added a solution of sodium methylate in methanol, as prepared from 0.6 g. of metallic sodium and 50 ml. of anhydrous methanol. The reaction mixture was then refluxed for several hours. The reaction product mixture was worked up by removing the solvent in vacuo to leave a residual oil which was chromatographed on a silica gel column, the elution being carried out with 5 percent acetone in toluene, There was collected 500 mg. of an oil which was identified by NMR spectrum and elemental analyses as 9-methoxy-9-(3-pyridyl)fluorene.

| Analyses calculated for $C_{19}H_{15}NO$: | | |
|---|---|---|
| | Theoretical | Found |
| C | 82.73% | 82.57% |
| H | 5.79 | 5.56 |
| N | 5.36 | 5.13 |

EXAMPLE 18

9-Chloro-9-(3-pyridyl)fluorene

A solution was prepared of 1.5 g. of 9-(3-pyridyl)-9-fluorenol and 50 ml. of benzene, to which was added 5 ml. of thionyl chloride. The reaction mixture was refluxed for about 2 hours. The benzene and excess thionyl chloride were removed in vacuo, leaving a residual oil. The oil was dissolved in methylene dichloride and triethylamine was added to the solution. The solution ws extracted with water. The methylene dichloride layer was dried over anhydrous sodium sulfate and concentrated in vacuo to yield about 500 mg. of an oil which was identified by NMR spectrum as 9-chloro-9-(3-pyridyl)fluorene.

EXAMPLE 19

α,α-Diphenyl-α-morpholino-3-pyridylmethane

To a solution of 15 g. of α,α-diphenyl-3-pyridinemethanol in 100 ml. of dichloromethane, there was added 25 ml. of thionyl chloride, and the mixture was refluxed for about 3 hours. The reaction mixture was concentrated in vacuo. The residue was washed with benzene and again concentrated in vacuo. The residue which was obtained was a yellow semi-solid, which was dissolved in 200 ml. of morpholine and the solution refluxed for about 3 hours. The reaction product mixture was cooled and concentrated to dryness in vacuo, leaving a residue. Water was added to the residue and the gray solids which separated were filtered off and dissolved in methylene dichloride. The methylene dichloride solution was washed with water, dried over anhydrous magnesium sulfate, and the drying agent was filtered off. The filtrate was concentrated in vacuo to yield a gray solid weighing about 16 g. This solid was recrystallized from hot acetone to yield product having a melting point of about 280° C. The product was identified by NMR spectrum and elemental analyses as α,α-diphenyl-α-morpholino-3-pyridylmethane.

| Analyses calculated for $C_{22}H_{22}N_2O$: | | |
|---|---|---|
| | Theoretical | Found |
| C | 79.97% | 80.01% |
| H | 6.71 | 6.77 |
| N | 8.48 | 8.09 |

EXAMPLE 20

α-(t-Butyl)-α-(4-chlorophenyl)α-(imidazol-1-yl)-3-pyridylmethane

The α-(t-butyl)-α-(4-chlorophenyl)-3-pyridinemethanol used as the starting material in this example was prepared according to the procedure of Example 13, supra, and identified by NMR spectrum.

Following the general procedure of Example 14, supra, there was then prepared α-(t-butyl)-α-chloro-α-(4-chlorophenyl)3-pyridylmethane for 15 g. of α-(t-butyl)-α-(4-chlorophenyl)-3-pyridinemethanol and 25 ml. of thionyl chloride in 150 ml. of toluene, and identified by NMR spectrum.

To the chloro compound, there was then added a solution of 15 g. of imidazole in 150 ml. of acetonitrile. The mixture was heated for several hours, the then the acetonitrile was removed in vacuo to leave a residue, and the crude residue was chromatographed over a silica gel column, the elution being carried out with a tolueneacetone mixture. Two compounds were isolated from the eluate. One compound was identified by NMR spectrum as α-(t-butyl)-α-(4-chlorophenyl)-3-[4-imidazol-1-yl)pyridinemethane]. The other compound had a melting point of about 112°–113° C., and was identified by microanalyses and NMR spectrum as α-(t- butyl)-α-(4-chlorophenyl)-α-(imidazol-1-yl)-3-pyridylmethane. Yield 2.5 g.

| Analyses calculated for $C_{19}H_{20}ClN_3$: | | |
|---|---|---|
| | Theoretical | Found |
| C | 70.04% | 70.24% |
| H | 6.19 | 5.90 |
| N | 12.90 | 13.15 |

EXAMPLE 21

α-(n-Pentoxy)-α-phenyl-3-pyridylmethane

A mixture of 11 g. of α-chloro-3-benzylpyridine, 20 g. of sodium pentoxide, and 100 ml. of dry benzene was refluxed for about 15 hours. The reaction product mixture was cooled and concentrated to dryness in vacuo. The residue was taken up in large amounts of ether and poured over crushed ice. The organic layer was separated, dried over anhydrous magnesium sulfate, and the drying agent filtered off. The filtrate was concentrated in vacuo and distilled at reduced pressure to yield product having a boiling point of about 125°–127° C./0.05 mm.; $\eta_D^{25}$ 1.5396. The product was identified by elemental analyses as α-n-pentoxy)-α-phenyl-3-pyridylmethane. Yield: 4. g.

| Analyses calculated for $C_{17}H_{21}NO$: | | |
|---|---|---|
| | Theoretical | Found |
| C | 79.96 | 79.40 |
| H | 8.29 | 8.10 |
| N | 5.49 | 5.68 |

EXAMPLE 22

α-(4-Chlorophenyl)-α-(4-chlorophenylthio)-3-pyridylmethane

A mixture of 12 g. of α-chloro-3-(4-chlorobenzyl)-pyridine, 8.5 g. of the sodium salt of 4-chlorothiophenol, and 100 ml. of dimethylformamide was refluxed for about 2 hours. The reaction product mixture was concentrated in vacuo and the residue taken up in 200 ml. of ether. The ether mixture was extracted with water. The water layer was extracted once with 100 ml. of benzene. The ether layer and the benzene layer were combined and dried over anhydrous magnesium sulfate. The drying agent was filtered off and the filtrate concentrated in vacuo and distilled at reduced pressure. The product obtained had a boiling point of about 180°–183° C./0.1 mm. and weighed 6 g. It had $\eta_D^{25}$ 1.6509. The product was identified by NMR spectrum and elemental analyses as α-(4-chlorophenyl)-α-(4-chlorophenylthio)-3-pyridylmethane. Yield: 6 g.

| Analyses calculated for $C_{18}H_{13}Cl_2NS$: | | |
|---|---|---|
| | Theoretical | Found |
| C | 62.43 | 62.24 |
| H | 3.78 | 3.84 |
| N | 4.04 | 3.89 |

Following the general procedure of Example 22, the following additional compound was prepared and identified. The compound, together with the principal starting materials and weights thereof used in the preparation, is listed in the example which follows.

EXAMPLE 23

α-(4-Chlorophenyl)-α-cyclohexylthio-3-pyridylmethane, having a boiling point of about 168°–174° C./0.1 mm., from 12 g. of α-chloro-3-(4-chlorobenzyl)pyridine and 7 g. of the sodium salt of cyclohexanethiol. Yield: 5.7 g.

| Analyses calculated for $C_{18}H_{20}ClNS$: | | |
|---|---|---|
| | Theoretical | Found |
| C | 68.00 | 67.82 |
| H | 6.34 | 6.33 |
| N | 4.59 | 4.45 |

EXAMPLE 24

α-(4-Chlorophenyl)-α-(n-pentylthio)-3-pyridylmethane

A mixture of 12 g. of α-chloro-3-(4-chlorobenzyl)-pyridine, 6 g. of the sodium salt of pentanethiol, and 100 ml. of tetrahydrofuran was refluxed for about 3 hours. Water was added to the reaction mixture and then the mixture was concentrated in vacuo to about one-fourth of its original volume. The residue was repeatedly extracted with ether. The ether extracts were combined, dried and concentrated in vacuo. The residue remaining was distilled at reduced pressure. There was obtained product having a boiling point of about 175°–180° C./0.75 mm., $\eta_D^{25}$ 1.5773. The product was identified by NMR and elemental analyses as α-(4-chlorophenyl)-α-(n-pentylthio)-3-pyridylmethane.

| Analyses calculated for $C_{17}H_{20}ClNS$: | | |
|---|---|---|
| | Theoretical | Found |
| C | 66.75 | 67.05 |
| H | 6.59 | 6.71 |
| N | 4.58 | 4.54 |

The novel method of this invention is practiced by adding the active substituted pyridine compounds to the water containing the submerged or floating aquatic weeds. The compounds may be applied to the water as dusts when admixed with a powdered solid carrier such as various mineral silicates, e.g., mica, talc, pyrophyllite, and clays. The compounds may be mixed with surface-active dispersing agents to form concentrates to facilitate dispersion in water and to improve the wetting properties when used as sprays. If desired, the compounds may be mixed with a powdered solid carrier, together with a surface-active dispersing agent, so that a wettable powder may be obtained which may be applied directly, or which may be shaken up with water to make an aqueous dispersion for application in that form. The compounds may be dissolved in an oil, such as hydrocarbon or chlorinated hydrocarbon oil, and the oil solution of the compound dispersed in water with the aid of a surface-active dispersing agent to give a sprayable aqueous dispersion. Such surface-active dispersing agents may be anionic, nonionic, or cationic surface-active agents. Such surface-active agents are well known, and reference is made to Hoffmann et al., U.S. Pat. No. 2,614,916, columns 2–4, for detailed examples of the same. The compounds useful in the present invention may also be applied by the aerosol method. Solutions for the aerosol treatment may be prepared by dissolving the compound directly in the aerosol carrier, which is a liquid under pressure, but which is a gas at ordinary temperature (e.g. 20° C.) and atmospheric pressure; or, the aerosol solution may be prepared by first dissolving the compound in a less volatile solvent, and then admixing such solution with the highly volatile liquid aerosol carrier.

The invention is practiced by adding to the water containing the submerged and floating weeds a growth-regulating and non-herbicidal amount of one of the hereindisclosed compounds, such that a concentration of from about 0.25 to about 10 ppm. of the active compound is attained.

The optimum concentration of active compound for any specific control problem varies with the temperature, the species to be controlled, and the shape of the body of water to be treated. At higher water temperatures, less compound is generally required for a given degree of control than is needed at lower temperatures.

In considering the treatment of moving streams for the purpose of controlling flora fixed therein, special account must be taken of the fact that the compounds will pass over the area to be treated and that the concentation during the contact period is dependent upon the water flow rate, the rate of chemical addition, and the period of addition.

The novel aquatic growth regulating method and compositions for use therein are illustrated by the following experiments.

Experiment 1

The following method was used in the laboratory to evaluate the aquatic growth regulating properties of the compounds disclosed herein, when used at a concentration of 10 ppm., against a representative submerged aquatic weed.

The compounds for this test were formulated in the following manner. Twenty mg. of compound was weighed into a 12 ml. disposable vial. To the vial containing the compound were added 1 ml. of acetone and 9 ml. of aqueous 0.1 percent polyoxyethylene sorbitan monooleate (Tween 80). To obtain the test concentration of 10 ppm., 4.00 ml. of this stock solution was added to 785 ml. of water in a plastic container. The plastic containers used were flowerpot-shaped, having a bottom diameter of 9 cm., a top diameter of 11.5 cm., and a height of 13.5 cm.

Terminal pieces of Florida elodea, *Hydrilla verticillata* (L.F.), (hereinafter identified as hydrilla) 10 cm. long, without branching, were prepared for testing. Three such cuttings were placed in each plastic container holding 785 ml. of water, to which water the formulated test compound had been added, along with 3 ml. of Hoagland's Nutrient solution. Three 10 cm. cuttings of hydrilla were placed in each of several control containers of water. To the water in each control container there was also added the amount of solvent used to formulate the test compound for each container.

After a period of two to three weeks, measurements were made to determine the total length of each plant. An average total growth was obtained by dividing the total combined lengths by the number of replicates. By subtracting 10 cm. from the average total length, the average increase in growth was obtained. This difference was divided by the average increase in length of the plants in the solvent controls (SC) and the quotient multiplied by 100 to give a percent inhibition.

$$\frac{\text{Total combined length of Replicates}}{\text{Number of Replicates}} = \text{Average Length}$$

Avg. Length − 10 cm. = Avg. Increased Growth $$\left(1 - \frac{\text{Avg. Increased Growth}}{\text{Avg. Increased Growth SC}}\right) \times 100 = \% \text{ Inhibition}$$

The compounds employed in this experiment, as well as in one or more of the experiments described hereinafter, are identified as follows:

1. 5-(β-Pyridyl)-5-hydroxynonane
2. 2-(β-Pyridyl)-2-heptanol
3. 2-(β-Pyridyl)-5-methyl-2-heptanol
4. 3-Pyridyl diphenylmethane
5. 3-[Bis(4-fluorophenyl)methyl]pyridine
6. α,α-Diphenyl-3-pyridinemethanol
7. α-t-Butyl-α-(4-chlorophenyl)-3-pyridinemethanol
8. α-Cyclopropyl-α-(4-chlorophenyl)-3-pyridinemethanol
9. 5-Hydroxy-5-(3-pyridyl)-10,11-didhydro-5-dibenzo[a,d]cycloheptene
10. 9-Hydroxy-9-(3-pyridyl)fluorene
11. α-Ethyl-α-phenyl-3-pyridinemethanol
12. α-(4-Chlorophenyl)-α-cyclopropyl-3-pyridinemethanol·HCl
13. α-Chloro-α-(3-pyridyl)-4,4'-dichlorodiphenylmethane
14. 9-(3-Pyridyl)fluorene
15. α-(3-Pyridyl)benzyl alcohol
16. α-Cyclobutyl-α-(4-methoxyphenyl)-3-pyridinemethanol
17. α-Cyclohexyl-α-(4-phenoxy-n-butyl)-3-pyridinemethanol
18. α-Cyclohexyl-α-(2-cyclohexylethyl)-3-pyridinemethanol
19. α-Isopropyl-α-(4-methoxyphenyl)-3-pyridinemethanol
20. α,α-Bis(3-pyridyl)benzyl alcohol
21. α-(2-Chlorophenyl)-3-pyridinemethanol
22. α-(2-Chlorophenyl)-α-methyl-3-pyridinemethanol.
23. α-(4-Chlorophenyl)-α-ethynyl-3-pyridinemethanol
24. α,α-Bis(n-pentyl)-3-pyridinemethanol·HCl
25. α-(n-Hexyl)-α-methyl-3-pyridinemethanol
26. α-Isopropyl-α-(4-propoxyphenyl)-3-pyridinemethanol
27. α-(2-Chlorophenyl)-α-(n-hexyl)-3-pyridinemethanol
28. α-(4-Chlorophenyl)-3-pyridinemethanol
29. α,α-Dibenzyl-3-pyridinemethanol
30. 9-(3-Pyridyl)thioxanthen-9-ol
31. α-(t-Butyl)-α-(4-propoxyphenyl)-3-pyridinemethanol
32. α-(p-Cumenyl)-α-isopropyl-3-pyridinemethanol
33. α-(t-Butyl)-α-(4-methoxyphenyl)-3-pyridinemethanol
34. α-Cyclohexylmethyl-3-pyridinemethanol
35. α-Cyclohexyl-α,α-bis(3-pyridyl)methanol
36. α,α-Bis(3-pyridyl)-n-nonanol
37. α,α-Bis(isobutyl)-3-pyridinemethanol 38. 3-[1-(2-Chlorophenyl)-n-heptyl]pyridine
39. 2-(3-pyridyl)-1-(4-chlorophenyl)-2-propanol
40. 3-(4,4'-Dichloro-α-ethoxydiphenylmethyl)pyridine
41. α-Cyclobutyl-α-(4-fluorophenyl)-3-pyridinemethanol
42. α-Pentafluorophenyl-α-phenyl-3-pyridinemethanol
43. 3-(α-Ethylbenzyl)pyridine
44. α-Phenyl-α-(2-thienyl)-3-pyridinemethanol
45. 9-(3-Pyridyl)-9-fluoreno·HCl 46. α-Propyl-α-(2-thienyl)-3-pyridinemethanol
47. α-Methyl-α-(4-phenoxyphenyl)-3-pyridinemethanol
48. α-(4-Chlorophenyl)-α-methyl-3-pyridinemethanol
49. α-(4-Bromophenyl)-2-ethyl-3-pyridinemethanol
50. α-Isopropyl-α-phenyl-3-pyridinemethanol
51. α,α-Bis(cyclopropyl(-3-pyridinemethanol·HCl
52. 5-(3-Pyridyl)-10,11-dihydro-5H-dibenzo[a,d]cycloheptene
53. 9-(3-Pyridyl)xanthen-9-ol
54. 9-(3-(Pyridyl)thioxanthen-9-ol
55. α,α-Bis(cyclohexy)-3-pyridinemethanol
56. 5-(3-Pyridyl)-5H-dibenzo[a,d]cyclohepten-5-ol·HCl
57. α-(4-Chlorophenyl)-α-cyclohexyl-3-pyridinemethanol·HCl
58. 3-(4-Chloro-α-isopropylbenzyl)pyridine
59. α,α-Diisopropyl-3-pyridinemethanol
60. α,α-Diisopentyl-3-pyridinemethanol·HCl
61. α-(n-Hexyl)-α-isobutyl-3-pyridinemethanol·HCl
62. α,α-Diphenyl-3-pyridineacetonitrile
63. α-(3-Ethyl-n-pentyl)-α-isobutyl-3-pyridinemethanol·HCl
64. α-Methyl-α-(n-nonyl)-3-pyridinemethanol
65. α,α-Bis(n-pentyl)-3-pyridinemethanol
66. α-(n-Heptyl)-α-isobutyl-3-pyridinemethanol
67. α-Cyclopropyl-α-(4-fluorophenyl)-3-pyridinemethanol
68. α,α-Bis(cyclohexylmethyl)-3-pyridinemethanol
69. α-Cyclohexyl-α-isopropyl-3-pyridinemethanol
70. α-(2,4-Difluorophenyl)-α-phenyl-3-pyridinemethanol
71. α-(4-Methoxyphenyl)-α-neopentyl-3-pyridinemethanol
72. α-Isopropyl-α-(α,α,α-trifluoro-m-tolyl)-3-pyridinemethanol
73. 3-(α,p-Dimethoxybenzyl)pyridine
74. α-(n-Hexyl)-α-isobutyl-3-pyridinemethanol
75. α-(n-Heptyl)-α-isopropyl-3-pyridinemethanol·HCl
76. 3-Butylpyridine
77. α-(n-Hexyl)-α-isopropyl-3-pyridinemethanol
78. α-(m-Chlorophenyl)-3-pyridinemethanol
79. 3-(α-t-Butyl)-α-(4-Chlorophenyl)-α-(Imidazol-1-yl)-3-pyridylmethane
80. α-Isopropyl-α-(3,4-xylyl)-3-pyridinemethanol
81. α-Isopropyl-α-(p-tolyl)-3-pyridinemethanol
82. α-Isopropyl-α-(m-tolyl)-3-pyridinemethanol
83. N-[Bis(4-chlorophenyl)-3-pyridylmethyl]acetamide
84. α-(Cyclohexylmethyl)-60-(n-octyl)-3-pyridinemethanol
85. α-(4-Chlorophenyl)-α-isopropyl-3-pyridinemethanol
86. α-(t-Butyl)-α-(4-fluorophenyl)-3-pyridinemethanol.
87. α-(t-Butyl)-α-chloro-α-(4-fluorophenyl)-3-pyridylmethane
88. α-(t-Butyl)-α-(4-fluorophenyl)-α-methoxy-3-pyridylmethane
89. α-sec.-Butyl-α-pentyl-3-pyridinemethanol
90. α-Heptyl-α-isopropyl-3-pyridinemethanol
91. α-(t-Butyl)-α-(4-fluorophenyl)-α-propoxy-3-pyridylmethane
92. 3-(9-Methoxyfluoren-9-yl)pyridine
93. 3-(9-Chlorofluoren-9-yl)pyridine
94. α-(4-Chlorophenyl)-α-(5-methyl-1,3-dioxan-5-yl)-3-pyridinemethanol·HCl
95. α-(5-Methyl-1,3-dioxan-5-yl)-α-phenyl-3-pyridinmethanol·HCl
96. α-(2,4-Dichlorophenyl-α-(1,3-dioxan-5-yl)-3-pyridinemethanol
97. α,α-Bis(4-chlorophenyl)-3-pyridinemethanol
98. α,α-Diphenyl-α-morpholino3-pyridylmethane
99. α-Isopropyl-α-[3,4-(methylenedioxy)phenyl]3-pyridinemethanol
100. α-(4-Chlorophenyl)-α-(n-pentylthio)-3-pyridinemethanol
101. α-(4-Chlorophenyl)-N,N-di(n-propyl)-3-pyridylmethylamine
102. α-(4-Chlorophenyl)-α-cyclohexylthio-3-pyridylmethane
103. α-(4-Chlorophenyl)-α-(4-chlorophenylthio)-3-pyridylmethane The results of the tests, run at a concentration of 10 ppm. of compound, and observed at the end of three weeks, are set forth in the table which follows. In the table, the number in column 1 identified the test compound; column 2 lists the percent growth inhibition of hydrilla observed.

Table 1

Substituted 3-Pyridine Derivatives

| Compound | Approx. % Growth Inhibition |
|---|---|
| 1 | 95 |
| 2 | 95 |
| 3 | 93 |
| 4 | 100 |
| 5 | 100 |
| 6 | 95 |
| 7 | 98 |
| 8 | 99 |
| 9 | 82 |
| 10 | 83 |
| 11 | 100 |
| 12 | 98 |
| 13 | 53 |
| 14 | 84 |
| 15 | 99 |
| 16 | 96 |
| 17 | 95 |
| 18 | 94 |
| 19 | 81 |
| 20 | 78 |
| 21 | 83 |
| 22 | 85 |
| 23 | 88 |
| 24 | 100 |
| 25 | 92 |
| 26 | 98 |
| 27 | 100 |
| 28 | 94 |
| 29 | 97 |
| 30 | 75 |
| 31 | 90 |
| 32 | 96 |
| 33 | 93 |
| 34 | 92 |
| 35 | 65 |
| 36 | 97 |
| 37 | 99 |
| 38 | 97 |
| 39 | 94 |
| 40 | 90 |
| 41 | 96 |
| 42 | 84 |
| 43 | 95 |
| 44 | 87 |
| 45 | 91 |
| 46 | 90 |
| 47 | 62 |
| 48 | 92 |
| 49 | 96 |
| 50 | 96 |
| 51 | 59 |
| 52 | 91 |
| 53 | 92 |
| 54 | 66 |
| 55 | 100 |
| 56 | 62 |
| 57 | 100 |
| 58 | 99 |
| 59 | 77 |
| 60 | 100 |
| 61 | 100 |
| 62 | 96 |
| 63 | 99 |
| 64 | 94 |
| 65 | 100 |

Table 1-continued
Substituted 3-Pyridine Derivatives

| Compound | Approx. % Growth Inhibition |
|---|---|
| 66 | 100 |
| 67 | 100 |
| 68 | 97 |
| 69 | 96 |
| 70 | 72 |
| 71 | 93 |
| 72 | 97 |
| 73 | 75 |
| 74 | 100 |
| 75 | 100 |
| 76 | 97 |
| 77 | 100 |
| 78 | 89 |
| 79 | 98 |
| 80 | 96 |
| 81 | 97 |
| 82 | 97 |
| 83 | 78 |
| 84 | 93 |
| 85 | 99 |
| 86 | 86 |
| 87 | 92 |
| 88 | 100 |
| 89 | 95 |
| 90 | 95 |
| 91 | 98 |
| 92 | 96 |
| 93 | 92 |
| 94 | 92 |
| 95 | 90 |
| 96 | 97 |
| 97 | 71 |
| 98 | 92 |
| 99 | 92 |
| 100 | 91 |
| 101 | 100 |
| 102 | 98 |
| 103 | 93 |

Experiment 2

The general procedure of Experiment 1 was repeated using a number of the same compounds at test concentrations of 1, 0.5 and 0.25 ppm.

The test compounds were formulated in the following manner: Twenty mg. of compound was weighed into a 12 ml. disposable vial. To the vial containing the compound were added 1 ml. of acetone and 9 ml. aqueous 0.1 percent polyoxyethylene sorbitan monooleate. This solution was designated as stock solution A.

The 1 ppm. test concentration was obtained as follows: Four ml. of stock solution A was diluted with 36 ml. of aqueous 0.1 percent polyoxyethylene sorbitan monooleate to give stock solution B. Four ml. of stock solution B, when added to 785 ml. water in the plastic test containers, gave a concentration of test compound of 1 ppm. The plastic test containers were identical to those employed to Experiment 1.

The 0.5 ppm. concentration of test compound was obtained as follows: Stock solution B, 20 ml., was diluted with 20 ml. aqueous 0.1 percent polyoxyethylene sorbitan monooleate, and this solution was designated stock solution C. Four ml. of stock solution C was added to 785 ml. of water in the plastic test containers to give a concentration of 0.5 ppm.

The 0.25 ppm concentration of test compound was obtained as follows: Stock solution C, 20 ml., was diluted with 20 ml. aqueous 0.1 percent polyoxyethylene sorbitan monooleate to give stock solution D. This stock solution D, 4 ml., added to 785 ml. of water in the plastic test containers gave a concentration of test compound of 0.25 pmm.

Three weeks after the date of application of the test compounds, measurements were made on the total growth of each plant, as described in Experiment 1, and the percent inhibition observed was calculated using the formulas set forth in Experiment 1, above. The results are recorded in the table which follows. The test compounds are each identified by the same number as used in Experiment 1.

Table 2
Substituted 3-Pyridine Derivatives

| Compound | Approx. % Growth Inhibition at Indicated Test Concentrations | | |
|---|---|---|---|
|  | 1 ppm. | 0.5 ppm. | 0.25 ppm. |
| 1 | 46 | 26 | 37 |
| 3 | 48 | 35 | 15 |
| 4 | 73 | 63 | 58 |
| 6 | 93 | 89 | 87 |
| 8 | 87 | 87 | 65 |
| 11 | 37 | 31 | 17 |
| 12 | 97 | 92 | 90 |
| 17 | 92 | 92 | 91 |
| 18 | 79 | 70 | 66 |
| 19 | 95 | 44 | 43 |
| 37 | 93 | 88 | 85 |
| 45 | 86 | 83 | 87 |
| 52 | 66 | 65 | 80 |
| 53 | 85 | 80 | 70 |
| 59 | 72 | 22 | 18 |
| 61 | −6 | 82 | 48 |
| 66 | 90 | 83 | 89 |
| 69 | 90 | 90 | 88 |
| 71 | 70 | 71 | 55 |
| 72 | 51 | 35 | 58 |
| 75 | 98 | 92 | 81 |
| 76 | 90 | 84 | 73 |
| 77 | 88 | 72 | 55 |
| 78 | 87 | 84 | 63 |
| 85 | 91 | 87 | 69 |
| 86 | 100 | 93 | 91 |
| 88 | 80 | 87 | 85 |
| 89 | 97 | 95 | 88 |
| 91 | 88 | 82 | 72 |
| 93 | 53 | 41 | 38 |
| 98 | 80 | 71 | 68 |
| 99 | 57 | 34 | 36 |
| 100 | 73 | 65 | 52 |
| 101 | 76 | 54 | 51 |
| 102 | 80 | 73 | 73 |
| 103 | 70 | 66 | 59 |

EXPERIMENT 3

A field test to establish the efficacy of selected compounds of the above formula as growth regulators of submerged and floating aquatic weeds was conducted in the following manner.

Individual tanks 3 feet in diameter and about 2 feet deep were each filled with 80 gallons of water. A layer of 4-6 inches of a mixture of sand-clay loam soil (50:50) was placed in the bottom of each tank. Three of the plants to be used in the test, namely Florida elodea, Southern naiad, and Eurasian milfoil, were prepared by cutting 4-inch terminal stems and burying the lower one inch of each stem in the soil in the tank. The surface of the soil was divided into four quadrants and each plant was planted in a separate quadrant. The plants were allowed a period of about two weeks to become rooted. About 10 days after these aquatic plants had been planted, 10 Gambusia affinis (mosquito fish) were added to each pool. About 4 days later, two sprigs of coontail were added to each pool, as well as sufficient duckweed to cover ¼ to ½ the water surface of each pool.

The compounds were tested at application rates of 2, 1 and 0.5 ppm. The test compounds were formulated by weighing 666.67 mg. (for 2ppm.), 333.34 mg. (for 1 ppm.), and 166.67 mg. (for 0.5 ppm.), and adding each weight to a mixture of 6 ml. of acetone and 54 ml. of aqueous 0.1 percent solution of Tween 80 (polyoxyethylene sorbitan monooleate). This provided approximately 60 ml. total volume of each formulation. There were two replicates per rate as well as six replicates, that is six pools, which received 60 ml. of the solvent, and 12 pools which served as untreated controls. Each pool was treated by pouring the 60 ml. of the formulated material directly into the pool and stirring the water to distribute the test compound.

The aquatic plants used in the test are identified by letters of the alphabet as follows:

A. Duckweed, *Lemna minor* L.
B. Coontail, *Ceratophyllum demersum* (L.)
C. Eurasian milfoil, *Myriophyllum specatum* L.
D. Florida elodea, *Hydrilla verticillate* (L.F.)
E. Southern naiad, *Najas quadalupensis* (Spreng.)

Observations of the growth regulation achieved by the test compounds were made at 3 weeks, 7 weeks, 10 weeks, and 12 weeks. The activity of the test compounds was compared in each case with the solvent controls. No fish toxicity was observed at any time throughout the period of the test. The growth inhibition was evaluated on a scale of 0 to 100 percent. As more than one determination was carried out at each rate, an average value was calculated.

The compounds employed in this field trial are identified by numbers, as set forth in Experiment 1.

The results of this field trial are recorded in Table 3, which follows. In the table, the number in column 1 identifies the test compound; column 2 indicates the application rate in parts per million (ppm.); column 3 indicates the weeks after treatment when the observation was made; and columns 4 through 8 list the approximate percent inhibition of the particular aquatic weed observed.

Table 3

| Cmp. | Appln. Rate ppm. | Weeks After Treatment | A | B | C | D | E |
|---|---|---|---|---|---|---|---|
| 6 | 2 | 3 | 100 | 100 | 60 | 100 | 100 |
|   | 1 |   | 100 | 100 | 60 | 100 | 100 |
|   | 0.5 |   | 100 | 100 | 60 | 90 | 100 |
|   | 2 | 7 | 100 | 100 | 40 | 100 | 100 |
|   | 1 |   | 100 | 100 | 20 | 100 | 100 |
|   | 0.5 |   | 100 | 100 | 15 | 90 | 100 |
|   | 2 | 10 | 100 | 100 | 40 | 100 | 100 |
|   | 1 |   | 100 | 100 | 0 | 100 | 100 |
|   | 0.5 |   | 100 | 100 | 0 | 90 | 100 |
|   | 2 | 12 | 100 | 100 | 0 | 100 | 100 |
|   | 1 |   | 100 | 100 | 0 | 99 | 100 |
|   | 0.5 |   | 100 | 100 | 0 | 93 | 100 |
| 12 | 2 | 3 | 100 | 100 | 100 | 100 | 100 |
|   | 1 |   | 100 | 100 | 90 | 100 | 90 |
|   | 0.5 |   | 100 | 100 | 80 | 100 | 90 |
|   | 2 | 7 | 100 | 100 | 100 | 100 | 100 |
|   | 1 |   | 100 | 100 | 80 | 100 | 100 |
|   | 0.5 |   | 100 | 100 | 60 | 100 | 100 |
|   | 2 | 10 | 100 | 100 | 100 | 100 | 100 |
|   | 1 |   | 100 | 100 | 30 | 100 | 100 |
|   | 0.5 |   | 100 | 100 | 10 | 100 | 100 |
|   | 2 | 12 | 100 | 100 | 98 | 100 | 100 |
|   | 1 |   | 100 | 100 | 20 | 100 | 100 |
|   | 0.5 |   | 100 | 100 | 0 | 100 | 100 |
| 37 | 2 | 3 | 100 | 100 | 100 | 100 | 100 |
|   | 1 |   | 100 | 100 | 100 | 100 | 100 |
|   | 0.5 |   | 100 | 100 | 95 | 90 | 100 |
|   | 2 | 7 | 100 | 98 | 100 | 100 | 100 |
|   | 1 |   | 100 | 83 | 100 | 70 | 100 |
|   | 0.5 |   | 100 | 95 | 85 | 15 | 100 |
|   | 2 | 10 | 100 | 100 | 100 | 100 | 100 |
|   | 1 |   | 100 | 100 | 100 | 70 | 100 |
|   | 0.5 |   | 100 | 100 | 100 | 5 | 100 |
|   | 2 | 12 | 100 | 100 | 100 | 99 | 100 |
|   | 1 |   | 100 | 100 | 99 | 55 | 100 |
|   | 0.5 |   | 100 | 100 | 98 | 0 | 100 |
| 74 | 2 | 3 | 100 | 65 | 100 | 95 | 95 |
|   | 1 |   | 100 | 50 | 100 | 90 | 70 |
|   | 0.5 |   | 100 | 45 | 80 | 75 | 45 |
|   | 2 | 7 | 100 | 78 | 85 | 95 | 100 |
|   | 1 |   | 100 | 60 | 75 | 65 | 98 |
|   | 0.5 |   | 100 | 60 | 10 | 35 | 80 |

Table 3-continued

| Cmp. | Appln. Rate ppm. | Weeks After Treatment | A | B | C | D | E |
|---|---|---|---|---|---|---|---|
|   | 2 | 10 | 100 | 100 | 10 | 10 | 75 |
|   | 1 |   | 100 | 100 | 0 | 5 | 60 |
|   | 0.5 |   | 100 | 100 | 0 | 0 | 45 |
|   | 2 | 12 | 100 | 100 | 0 | 0 | 50 |
|   | 1 |   | 100 | 100 | 0 | 0 | 50 |
|   | 0.5 |   | 100 | 100 | 0 | 0 | 35 |
| 76 | 2 | 3 | 0 | 10 | 10 | 10 | 10 |
|   | 1 |   | 0 | 0 | 0 | 0 | 0 |
|   | 0.5 |   | 0 | 0 | 0 | 0 | 0 |
| 85 | 2 | 3 | 100 | 100 | 100 | 100 | 100 |
|   | 1 |   | 100 | 100 | 100 | 100 | 100 |
|   | 0.5 |   | 100 | 100 | 100 | 100 | 100 |
|   | 2 | 7 | 100 | 100 | 100 | 100 | 100 |
|   | 1 |   | 100 | 100 | 100 | 100 | 100 |
|   | 0.5 |   | 100 | 100 | 95 | 100 | 100 |
|   | 2 | 10 | 100 | 100 | 100 | 100 | 100 |
|   | 1 |   | 100 | 100 | 98 | 100 | 100 |
|   | 0.5 |   | 100 | 100 | 80 | 95 | 100 |
|   | 2 | 12 | 100 | 100 | 100 | 100 | 100 |
|   | 1 |   | 100 | 100 | 97 | 100 | 100 |
|   | 0.5 |   | 100 | 100 | 50 | 95 | 100 |
| SC* | 0 | 3 | 0 | 0 | 0 | 0 | 0 |
|   | 0 | 7 | 60 | 0 | 0 | 0 | 0 |
|   | 0 | 10 | 99 | 100 | 0 | 0 | 0 |
|   | 0 | 12 | 100 | 100 | 0 | 0 | 0 |

*SC - Solvent Control

EXPERIMENT 4

A study was conducted of the time exposure effect of α-(4-chlorophenyl)-α-isopropyl-3-pryrinemethanol on Florida elodea (*Hydrilla verticillata*), hereinafter referred to as hydrilla. The procedure and materials used in this study are described as follows.

Twelve battery jars were set up, with each jar containing 1000 ml. of dechlorinated tap water. To the water in each jar there was added 4 ml. of Hoagland's Nutrient solution and 24 cuttings of hydrilla, each cutting being 10 cm. in length. The test compound was formulated by weighing out weights of 20 mg., 10 mg., and 2 mg., and each of these weights of compound was then dissolved in 1 ml. of acetone plus 9 ml. of aqueous 0.1 percent polyoxyethylene sorbitan monooleate, yielding three solutions having a volume of 10 ml. each. Each solution was divided equally between two battery jars to give two battery jars containing 10 ppm. of test compound, two battery jars containing 5 ppm. of test compound, and two battery jars containing 1 ppm. of test compound. The remaining six battery jars were divided into three groups, each containing two jars, and an amount of solvent equivalent to that used to give the formulations of 10, 5 and 1 ppm., respectively, was added to the jars of each group, to serve as solvent controls.

Three plants were removed from each jar into a 750 ml. plastic carton containing 750 ml. of dechlorinated tap water plus 3 ml. of Hoagland's nutrient solution and 4 ml. of aqueous 0.1 percent Tween 80 (polyoxyethylene sorbitan monooleate) solution at time intervals equal to approximately 10 minutes, 3 hours, 6 hours, 12 hours, 24 hours, 48 hours, and 72 hours. Left remaining in the battery jars were three plant cuttings for a continuous exposure of 3 weeks to the test compound or to the solvent controls. Weekly measurements were made of the plants to determine the total length of each plant. The calculations of the percent inhibition observed were carried out using the formula disclosed in Experiment 1, above. The results of the tests, as calculated at the end of 1 week, 2 weeks and 3 weeks, are set forth in the table which follows. In the table, column 1 identifies the time of exposure of the plant to the test compound;

column 2, the percent growth inhibition of hydrilla observed in the solvent controls; column 3, the percent growth inhibition of hydrilla observed at the application rate of 1 ppm.; column 4, the percent growth inhibition observed at application rate of 5 ppm.; and column 5, the percent growth inhibition of hydrilla observed at an application rate of 10 ppm. The table is divided into three parts in order to record the percent inhibition observed at the end of 1 week, 2 weeks and 3 weeks.

Table 4

| Exposure Time | % Inhibition Observed Weekly at Indicated Application Rate | | | |
|---|---|---|---|---|
| | SC | 1 ppm. | 5 ppm. | 10 ppm. |
| 1 week | | | | |
| 10 min. | 0 | 46 | 40 | 46 |
| 3 hr. | 0 | 49 | 42 | 54 |
| 6 hr. | 0 | 43 | 51 | 49 |
| 12 hr. | 0 | 57 | 60 | 67 |
| 24 hr. | 0 | 66 | 75 | 73 |
| 48 hr. | 0 | 63 | 80 | 80 |
| 72 hr. | 0 | 74 | 82 | 81 |
| continuous | 0 | 75 | 89 | 89 |
| 2 weeks | | | | |
| 10 min. | 0 | 37 | 38 | 48 |
| 3 hr. | 0 | 43 | 53 | 64 |
| 6 hr. | 0 | 41 | 70 | 67 |
| 12 hr. | 0 | 47 | 71 | 77 |
| 24 hr. | 0 | 56 | 80 | 81 |
| 48 hr. | 0 | 55 | 81 | 85 |
| 72 hr. | 0 | 66 | 85 | 87 |
| continuous | 0 | 89 | 96 | 98 |
| 3 weeks | | | | |
| 10 min. | 0 | 22 | 23 | 34 |
| 3 hr. | 0 | 37 | 52 | 60 |
| 6 hr. | 0 | 36 | 74 | 70 |
| 12 hr. | 0 | 45 | 73 | 83 |
| 24 hr. | 0 | 48 | 79 | 84 |
| 48 hr. | 0 | 55 | 85 | 90 |
| 72 hr. | 0 | 60 | 88 | 92 |
| continuous | 0 | 92 | 97 | 100 |

The results of this experiment indicate that the test compound, α-(4-chlorophenyl)-α-isopropyl-3-pyridinemethanol, is rapidly taken up by *Hydrilla verticillata*, and 10 minutes of exposure to the compound is sufficient to achieve considerable inhibition of growth for about a week. Longer exposure, of course, promotes inhibition of growth for longer periods of time.

The results obtained in the experiments described and reported above show that the 3-substituted pyridine compound disclosed herein are effective in the claimed method of regulating the growth of submerged and floating aquatic weeds.

I claim:

1. A method for inhibiting the growth of submerged and floating aquatic weeds which comprises adding to the water containing said weeds an amount sufficient to provide a growth-regulating and non-herbicidal concentration of a compound of the formula

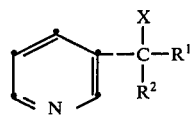

wherein
X is hydrogen, hydroxyl, halo, $C_1$-$C_3$ alkoxy, $C_1$-$C_6$ alkylthio, cyclohexylthio, 4-chlorophenylthio, —N($R^3$)$_2$, acetamido, imidazol-l-yl, morpholino, or cyano;
$R^1$ is hydrogen, $C_1$-$C_9$ alkyl, ethynyl, $C_3$-$C_6$ cycloalkyl, benzyl, phenyl, or monohalophenyl;
$R^2$ is $C_1$-$C_9$ alkyl, $C_3$-$C_6$ cycloalkyl, cyclohexylmethyl, cyclohexylethyl, phenyl, monohalophenyl, dihalophenyl, 3,4-(methylenedioxy)phenyl, trifluoromethylphenyl, p-cumenyl, tolyl, phenoxyphenyl, phenoxy($C_1$-$C_4$)alkyl, benzyl, $C_1$-$C_4$ alkoxyphenyl, pentafluorophenyl, xylyl, 2-thienyl, 3-pyridyl, 1,3-dioxan-5-yl, or 5-methyl-1,3-dioxan-5-yl; and
$R^1$ and $R^2$, when taken together with the carbon atom to which they are attached, form 2,6-dimethylcyclohexan-1-yl, 9-fluorenyl, 10,11-dihydro-5H-dibenzo[a,d]cyclohepten-5-yl, 9-xanthenyl, 5H-dibenzo[a,d]cyclohepten-5-yl, or 9-thioxanthenyl;
$R^3$ is hydrogen or $C_1$-$C_6$ alkyl; and
the nonphytotoxic acid addition salts thereof.

2. The method of claim 1 wherein the growth-regulating and non-herbicidal concentration of the active compound ranges from about 0.25 to about 10 ppm.

3. The method of claim 1 wherein the active compound is of the formula

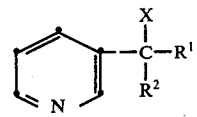

wherein
X is hydrogen, hydroxyl or methoxy;
$R^1$ is hydrogen, $C_1$-$C_8$ alkyl, $C_3$-$C_6$ cycloalkyl, or phenyl;
$R^2$ is $C_1$-$C_8$ alkyl, cyclohexylmethyl, cyclohexyl, phenyl, 4-fluorophenyl, 4-chlorophenyl, 4-methoxyphenyl, p-tolyl, or 4-phenoxy-n-butyl;
$R^1$ and $R^2$, when taken together with the carbon atom to which they are attached, form 9-fluorenyl, 9-xanthenyl, or 10,11-dihydro-5H-dibenzo[a,d]cyclohepten-5-yl; and
the nonphytotoxic acid addition salts thereof.

4. The method of claim 1 wherein the active compound is of the formula

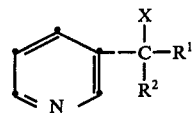

wherein
X is hydrogen, hydroxyl or methoxy;
$R^1$ is $C_3$-$C_8$ alkyl, cyclopropyl, cyclohexyl, or phenyl;
$R^2$ is $C_4$-$C_7$ alkyl, 4-chlorophenyl, 4-fluorophenyl, 4-methoxyphenyl, p-tolyl, cyclohexylmethyl, phenyl, and 4-phenoxy-n-butyl;
$R^1$ and $R^2$, when taken together with the carbon to which they are attached, form 9-fluorenyl; and
the nonphytotoxic acid addition salts thereof.

5. The method of claim 1 wherein the active compound is of the formula

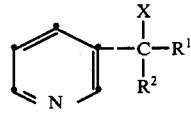

wherein
X is hydroxyl;
$R^1$ is isopropyl, cyclopropyl, isobutyl, t-butyl, or phenyl;

R² is n-hexyl, phenyl, 4-fluorophenyl, 4-methoxyphenyl, or 4-chlorophenyl; and the nonphytotoxic acid addition salts thereof.

6. The method of claim 1 wherein the active compound is α,α-diphenyl-3-pyridinemethanol.

7. The method of claim 1 wherein the active compound is α-(4-chlorophenyl)-α-cyclopropyl-3-pyridinemethanol hydrochloride.

8. The method of claim 1 wherein the active compound is α,α-diisobutyl-3-pyridinemethanol.

9. The method of claim 1 wherein the active compound is α-hexyl-α-isobutyl-3-pyridinemethanol.

10. The method of claim 1 wherein the active compound is α-(4-chlorophenyl)-α-isopropyl-3-pyridinemethanol.

11. The method of claim 1 wherein the active compound is 3-pyridyl diphenylmethane.

12. The method of claim 1 wherein the active compound is α-isopropyl-α-(4-methoxyphenyl)-3-pyridinemethanol.

13. The method of claim 1 wherein the active compound is α-(t-butyl)-α-(4-fluorophenyl)-3-pyridinemethanol.

* * * * *

UNITED STATES PATENT OFFICE
CERTIFICATE OF CORRECTION

Patent No. 4,116,665          Dated   September 26, 1978

Inventor(s)  Eriks V. Krumkalns

It is certified that error appears in the above-identified patent and that said Letters Patent are hereby corrected as shown below:

Column 1, line 18:   "series" should read --serious--.

Column 1, line 55:   "Apr. 11, 1972)" should read --(Apr. 11, 1972)--.

Column 3, line 60:   "3-$C_6$" should read --$C_3$-$C_6$--.

Column 12, line 4:   "ws" should read --was--.

Column 12, line 59:  "the then the" should read --and then the--.

Column 12, line 63:  "tolueneacetone" should read --toluene acetone--.

Column 12, line 66:  "imidazol-1" should read --(imidazol-1--.

Column 13, line 25:  "n-pentoxy)" should read --(n-pentoxy)--.

Column 16, line 20:  "didhydro" should read --dihydro--.

Column 16, line 59:  "38. 3-[1-(2-" should start a new line on line 60 with Chlorophenyl directly following --38. 3-[1-(2- --.

Column 16, line 68:  "fluoreno" should read --fluorenol--.

Column 17, line 10:  "(Pyridyl)" should read --Pyridyl)--.

Column 17, line 11:  "(cyclohexy)" should read --(cyclohexyl)--.

Column 17, line 19:  "Dipehnyl" should read --Diphenyl--.

UNITED STATES PATENT OFFICE
CERTIFICATE OF CORRECTION

Patent No. 4,116,665      Dated September 26, 1978

Inventor(s) Eriks V. Krumkalns

It is certified that error appears in the above-identified patent and that said Letters Patent are hereby corrected as shown below:

Column 17, line 47: "(Cyclohexylmethyl)-60-" should read --(Cyclohexylmethyl)-α--.

Column 17, line 65: "pyridinemthanol" should read --pyridinemethanol--.

Column 19, line 66: "pmm" should read --ppm--.

Column 21, line 14: "verticillate" should read --verticillata--.

Column 21, line 15: "quadalupensis" should read --guadalupensis--.

Signed and Sealed this

Twenty-ninth Day of May 1979

[SEAL]

Attest:

RUTH C. MASON
Attesting Officer

DONALD W. BANNER
Commissioner of Patents and Trademarks